United States Patent

Oraevsky et al.

[11] Patent Number: 5,840,023
[45] Date of Patent: Nov. 24, 1998

[54] OPTOACOUSTIC IMAGING FOR MEDICAL DIAGNOSIS

[76] Inventors: Alexander A. Oraevsky, 5038 Lymbar Dr., Houston, Tex. 77096; Steven L. Jacques, 4302 Compton Cir., Bellaire, Tex. 77401; Rinat O. Esenaliev, 7600 Kirby, Apt. 401, Houston, Tex. 77030

[21] Appl. No.: 594,758

[22] Filed: Jan. 31, 1996

[51] Int. Cl.⁶ ..................................................... A61B 8/00
[52] U.S. Cl. ................................ 600/407; 606/3; 73/587; 73/606; 367/7
[58] Field of Search ................................. 128/653.1, 664, 128/665, 633, 660.01; 356/318, 346, 432; 250/351, 340, 341.1; 378/86, 87, 901, 21, 22, 64; 367/7; 73/606, 587; 607/89; 600/407, 473, 476, 310, 437; 601/3, 4; 606/2, 2.5, 3

[56] References Cited

U.S. PATENT DOCUMENTS

| | | |
|---|---|---|
| 4,028,933 | 6/1977 | Lemons et al. . |
| 4,212,206 | 7/1980 | Hartemann et al. ....................... 73/606 |
| 4,430,897 | 2/1984 | Quate ......................................... 73/606 |
| 4,710,030 | 12/1987 | Tauc et al. . |
| 4,727,420 | 2/1988 | Kohda et al. . |
| 5,041,121 | 8/1991 | Wondrazek et al. . |
| 5,136,172 | 8/1992 | Nataka et al. ........................... 250/572 |
| 5,141,331 | 8/1992 | Oehler et al. ............................ 374/118 |
| 5,178,836 | 1/1993 | Kitamori et al. ......................... 422/73 |
| 5,254,112 | 10/1993 | Sinofsky et al. ............................. 606/7 |
| 5,293,873 | 3/1994 | Fang . |
| 5,398,685 | 3/1995 | Wilk et al. . |
| 5,421,337 | 6/1995 | Richards-Kortum et al. . |
| 5,465,722 | 11/1995 | Fort et al. . |
| 5,582,578 | 12/1996 | Zhong et al. . |
| 5,583,634 | 12/1996 | Andre et al. . |
| 5,602,894 | 2/1997 | Bardash . |
| 5,615,675 | 4/1997 | O'Donnell et al. . |

*Primary Examiner*—Marvin M. Lateef
*Assistant Examiner*—Shawna J. Shaw
*Attorney, Agent, or Firm*—Benjamin Aaron Adler

[57] ABSTRACT

The laser optoacoustic imaging system described herein utilizes time-resolved measurement of profiles of laser-induced transient pressure (acoustic) waves. The pressure waves are emitted by acoustic sources preferentially generated in absorbing tissues of diagnostic interest. This technique allows visualization of absorbed light distribution in turbid, layered and heterogeneous tissues irradiated by laser pulses in vivo. The laser optoacoustic tomography can be used for the characterization of structure and properties of normal tissue, and for the detection of tissue pathological changes. The optical heterogeneities that can be imaged with the laser optoacoustic imaging system include abnormal tissues such as tumors, injured tissues, blood vessels and other layered tissues. Further, three dimensional images of organs and portions of organs can be obtained.

28 Claims, 6 Drawing Sheets

OPTOACOUSTIC IMAGING FOR MEDICAL DIAGNOSIS

BACKGROUND OF THE INVENTION

1. Field of the Invention

The present invention relates generally to the fields of optics, lasers and medical diagnostic devices. More specifically, the present invention relates to a laser optoacoustic imaging system capable of producing a three-dimensional image (tomography scan) of human organs.

2. Description of the Related Art

Ultrasonic imaging is currently used widely in clinical medical practice to detect abnormalities in soft tissue organs with acoustic boundaries such as one type of tissue embedded within another type. Ultrasonic imaging has, however, several limitations. For example, ultrasonic imaging is incapable of detecting acoustically homogeneous tissues, i.e., when ultrasonic properties of all of the tissues scanned are similar).

Optical imaging technologies are based on time-resolved or phase-resolved detection of diffusely reflected light pulses or photon density waves. Optical tomographic technologies take advantage of differences in tissue optical properties for diagnostic purposes. However, ubiquitous light scattering in tissues has been a great obstacle to laser imaging.

Optoacoustic spectroscopy methods utilize light to excite an object of interest (molecules or atoms). Using acoustic (piezoelectric) detectors, optoacoustic spectroscopy methodology can measure stress amplitude for obtaining absorption spectra. This represents not an imaging or tomographic technology per se.

Principles of laser optoacoustics, i.e., methods of stress generation and detection have been described. Relationships between spatial distribution of acoustic sources and temporal profile of laser-induced stress waves have been derived. However, methods of laser optoacoustics have not been proposed as means for medical diagnostics.

The prior art is deficient in the lack of functional laser opto-acoustic imaging system. The present invention fulfills this longstanding need and desire in the art.

SUMMARY OF THE INVENTION

Photo-acoustic ultrasound technology for medical imaging has been described in the prior art. However, the prior art has not understood and correctly manipulated three principles of laser optoacoustic imaging important for sensitivity, spatial resolution and correct interpretation of images. These principles are: (1) short-pulse laser irradiation to generate transient stress waves under conditions of temporal stress confinement. Such irradiations provides the highest possible amplitude of generated stress with profiles resembling that of light distribution in tissues, which yields sharp images with accurate localization; (2) time-resolved detection of a stress profile for obtaining diagnostic information not from the fact of any signal detection, but from the temporal profile of generated stress wave; (3) use of wideband piezoelectric detectors to correctly reproduce stress profiles (acoustic waves with wide spectrum of ultrasonic frequencies) to obtain high spatial resolution of tomography. The laser opto-acoustic imaging system (LOAIS) of the present invention partially combines elements of (1) ultrasonic scanning, (2) optical time-resolved tomography and (3) selective pulsed excitation of tissue heterogeneous structures and time-resolved detection of laser-induced stress waves for obtaining detailed medical diagnostic information.

The present invention is directed to both a technique and a device and can be used to image a complex tissue structure on the basis of optical contrast. The technique of the present invention uses a pulsed laser to slightly but quickly heat a specific tissue region with an optical obsorption that differs relative to its surroundings. This slight heating converts to a pressure wave, i.e, a sound wave which propagates outward from the source of the heating. A transducer detects the time, magnitude and shape of the arriving pressure waves. The transducer may be a piezoelectric transducer at the tissue surface or an imbedded transducer. The laser pulse must be sufficiently short to allow the pressure to build up before the pressure can dissipate at the speed of sound (approximately 1500 m/s). For example, a 10-ns laser pulse can image absorbing objects with the spatial resolution of (1500 m/s) (10 ns)=15 $\mu$m. Thus, the invention allows imaging of tissue structures with high spatial resolution within turbid media such as biological tissues. The imaging techniques of the present invention are based on optical contrast rather than density changes such as in ultrasound, magnetic resonance imaging or x-ray computed tomography. The method of the present invention, therefore, can be used to image contrast objects not well imaged by these other state of the art imaging techniques.

In one embodiment of the present invention, there is provided a method of diagnosing a diseased tissue within a normal tissue using laser optoacoustic tomography, comprising the steps of: irradiating the surface of the normal tissue with at least one laser pulse so as to penetrate to a sufficient depth and selectively heat a small volume or layer of diseased tissue with a higher optical absorption; causing the diseased tissue to produce a stress wave with a profile resembling that of diseased tissue, said stress wave propagates with minimal alterations to the surface of normal tissue; detecting said stress wave with at least one acoustic transducer; recording the amplitude and temporal profile of laser-induced stress wave by digital oscilloscope; analyzing the amplitude and temporal profile of laser-induced stress wave with a computer.

In another embodiment of the present invention, there is provided a novel device as a tomography system for biomedical diagnostics comprising: a pulsed laser; a light delivery system; at least one acoustic detector; an electronic system for signal recording and processing; and a computer with software for image reconstruction and analysis.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

Definitions

Figure 1:
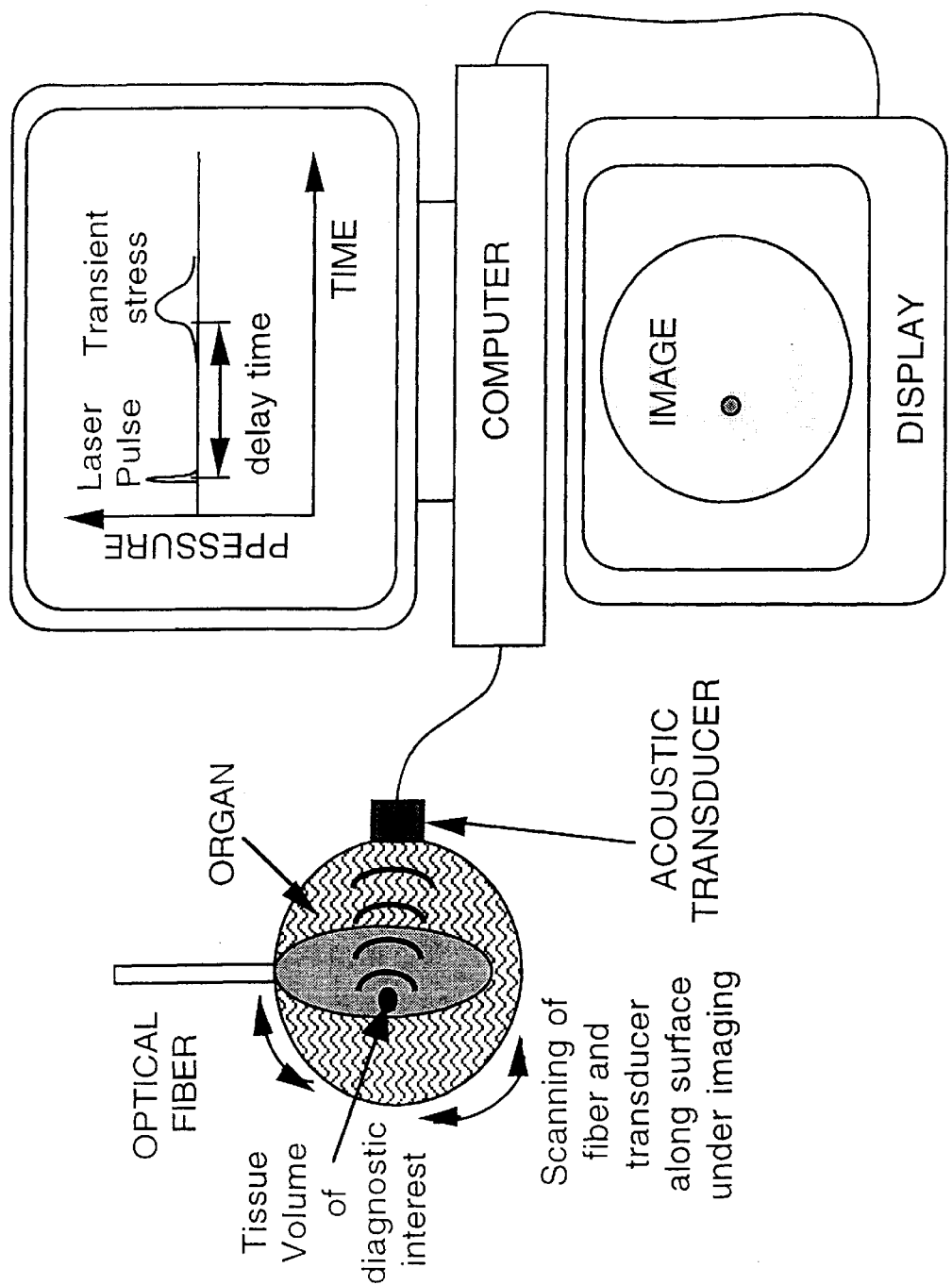
FIG. 1 shows a schematic of the laser optoacoustic tomography system in transmission mode.

As used herein, the term "laser optoacoustic tomography" refers to a laser optoaccoustic tomography system that employs detection of stress waves reflected from the volume of their generation back to the irradiated tissue surface. In other words, laser optoaccoustic tomography is a diagnostic procedure to obtain optical images of layered tissue while detecting laser induced stress profiles.

As used herein, the term "tomography in reflection transmission mode" refers to the laser optoaccoustic tomography system of the present invention that employs the detection of stress waves transmitted from the volume of their generation to rear tissue surfaces, i.e., opposite to irradiated.

As used herein, the term "transient stress waves" refers to a stress wave that has limited duration and occupies limited volume.

As used herein, the term "temporal stress confinement" refers to the confinement of laser-induced stress within heated volume during the course of laser energy deposition.

As used herein, the term "time-resolved detection of stress profile" refers to the detection of transient stress waves with temporal resolution sufficient to reconstruct a pressure wave profile with precision.

As used herein, the term "optical time-resolved tomography" refers to a tomography based on time-resolved detection of ultrashort laser pulses transmitted through biological tissue of diagnostic interest.

As used herein, the term "piezoelectric detectors" refers to detectors of accoustic, e.g., stress waves utilizing the principle of electric charge generation upon a change of volume within crystals subjected to a pressure wave.

As used herein, the term "ultrasonic scanning" refers to a diagnostic procedure that employs delivery of ultrasonic stress waves to a tissue surface followed by the detection of the signals reflected from boundries within the tissue under diagnosis.

As used herein, the term "pulsed heating of tissue" refers to the heating of a tissue volume irradiated with laser pulses.

The present invention utilizes the time-resolved detection of laser-induced stress (ultrasonic) waves to obtain tomography images of human organs or cellular structures for diagnostic purposes. Diagnostic procedures in which the laser opto-acoustic imaging system of the present invention are useful include: (1) short laser pulses delivered to the front surface of human organ under investigation. Laser wavelength must be selected to achieve desirable light penetration depth and maximum contrast between normal and abnormal tissues. Heterogeneous absorption of photons and heating of tissue causes generation of thermo-elastic stress that is temporarily confined in the irradiated volume. Short laser pulses serve three purposes: (1) obtain the most effective generation of transient stress, (2) obtain a stress profile which resembles the profile of heterogeneous light distribution, (3) to obtain images with ultimate accuracy of localization of tissue layer or volume of diagnostic interest.

Transient stress waves will propagate toward acoustic transducer (detector). A transducer, e.g., a piezoelectric transducer, will convert the stress profile into an electrical signal. The temporal profile of the electrical signal recorded by a digital oscilloscope is converted into a spatial profile of a transient stress distribution. Transient stress distribution resembles a profile of absorbed laser energy distribution, which in turn carries certain diagnostic information. Both a laser beam and a piezoelectric transducer (detector) are scanned over the area under diagnosis. Positioning of a detector at various locations permits reconstruction of a three dimensional opto-acoustic image from transient stress profiles and time-delays between moments of laser pulsed irradiation and moments of stress detection (the speed of acoustic waves propagation is known for vast majority of tissues). Stress detection can be performed in both, the transmission mode and the reflection mode, which allows substantial flexibility for in vivo diagnostics of various human organs and other biological systems.

Laser opto-acoustic imaging systems (LOAIS) can be used in diagnostic screening of breast cancer (mammography), skin tumors and various other lesions (like port-wine stains etc.) whether accessible externally or via endoscopes, detection of brain hematomas (hemorrhages), atherosclerotic lesions in blood vessels, and for general characterization of tissue composition and structure. In addition, laser opto-acoustic imaging can provide feedback information during laser medical treatments.

Thus, the present invention is directed to a method of diagnosing a diseased tissue within a normal tissue using laser optoacoustic tomography, comprising the steps of: irradiating the surface of the normal tissue with at least one laser pulse so as to penetrate to a sufficient depth and selectively heat a small volume or layer of diseased tissue with a higher optical absorption; causing the diseased tissue to produce a stress wave with a profile resembling that of diseased tissue, said stress wave propagates with minimal alterations to the surface of normal tissue; detecting said stress wave with at least one acoustic transducer; recording the amplitude and temporal profile of laser-induced stress wave by digital oscilloscope; analyzing the amplitude and temporal profile of laser-induced stress wave with a computer.

Preferably, the stress profiles are recorded and analyzed by the computer to reconstruct a three-dimensional image. Generally, the laser pulse heats certain tissue structures with different light absorption thereby generating stress profiles resembling profiles of absorbed laser energy distribution in heterogeneous tissues followed by time-resolved detection of ultrasonic stress waves. The shape and dimensions of the diseased tissue volume or layer is generally determined from the temporal profile of laser-induced stress, the time of stress wave arrival to the accoustic transducer, and the direction of the stress detection.

Preferably, the accoustic transducer is a piezoelectric detector and the acoustic transducer uses temporal resolution. Ordinarily, the transducer determines the geometry of the diagnosed tissue volume without scanning of acoustic transducer at a fixed location of the laser beam. However, multiple separate optical fibers or laser beams can be used to irradiate large volume of tissue to reduce time of scanning and incident laser fluence. Generally, the amplitude and temporal profile of laser-induced stress wave is recorded by a digital oscilloscope.

In the methods of the present invention, stress detection can be in transmission mode and stress detection of tissue optical heterogeneities occurs at a tissue depth of up to about 12 cm. Alternatively, stress detection can be in reflection mode. Generally, the irradiating is in spectral range of therapeutic window from about 600 nm to about 1400 nm. It is further contemplated that one with ordinary skill in this art could use exogenous molecular probes or dyes to enhance contrast of tomographic image.

Generally, the methods of the present invention may be used to diagnose a wide variety of diseased tissue. Preferably, the diseased tissue is breast carcinoma, brain hemorrhages, hematomas, atherosclerotic plaques, polyarhtritis, port-wine stains, skin disorders, melanomas or ocular diseases.

When the diseased tissue is an internal organ, the irradiation may be delivered via an endoscope and the acoustic transducer may be positioned on the skin surface. Alternatively, the irradiation may be delivered onto the skin surface and the transducer is incorporated with an endoscope and positioned inside the organs. Further, when the diseased tissue is an internal organ, the optical fiber and transducer may be incorporated in endoscope and positioned inside the organs.

The present invention also provides a novel device as a tomography system for biomedical diagnostics comprising: a pulsed laser; a light delivery system; at least one acoustic detector; an electronic system for signal recording and processing; and a computer with software for image reconstruction and analysis.

The following examples are given for the purpose of illustrating various embodiments of the invention and are not meant to limit the present invention in any fashion.

With reference to the appended drawings, FIG. 1 illustrates one embodiment of the present invention, i.e., an example of the utility of laser optoacoustic tomography in diagnosing a small diseased tissue volume (black circle) within a large volume of normal tissue. The laser pulse irradiates the surface of the normal tissue and penetrates to a sufficient depth to selectively heat a small volume of diseased tissue with a higher optical absorption. Instantly, the heated volume of diseased tissue produces a stress wave with a profile resembling that of diseased tissue. The stress wave propagates with minimal alterations to the surface of normal tissue where it is detected by an acoustic transducer with temporal resolution. The amplitude and temporal profile of laser-induced stress wave is recorded by digital oscilloscope and transferred via an interface to a computer for data analysis. Scanning of laser beam (optical fiber) allows the irradiation of the entire volume of the tomographically scanned organ and definite heating of any diseased tissues that exist within normal tissue. Scanning of the acoustic transducer along the surface of the organ permits a determination of the exact location of any diseased tissue volumes. The stress profiles are recorded and analyzed by the computer to reconstruct three dimensional images which can be displayed.

Tomography (imaging) in stress transmission mode utilizes detection of stress transients transmitted from the laser-excited volume toward the depth through thick layers of tissue. The emphasis in transmission mode tomography is made on sensitive detection of tissue optical heterogeneities located at substantial depth of tissue (up to 12 cm).

Figure 2:
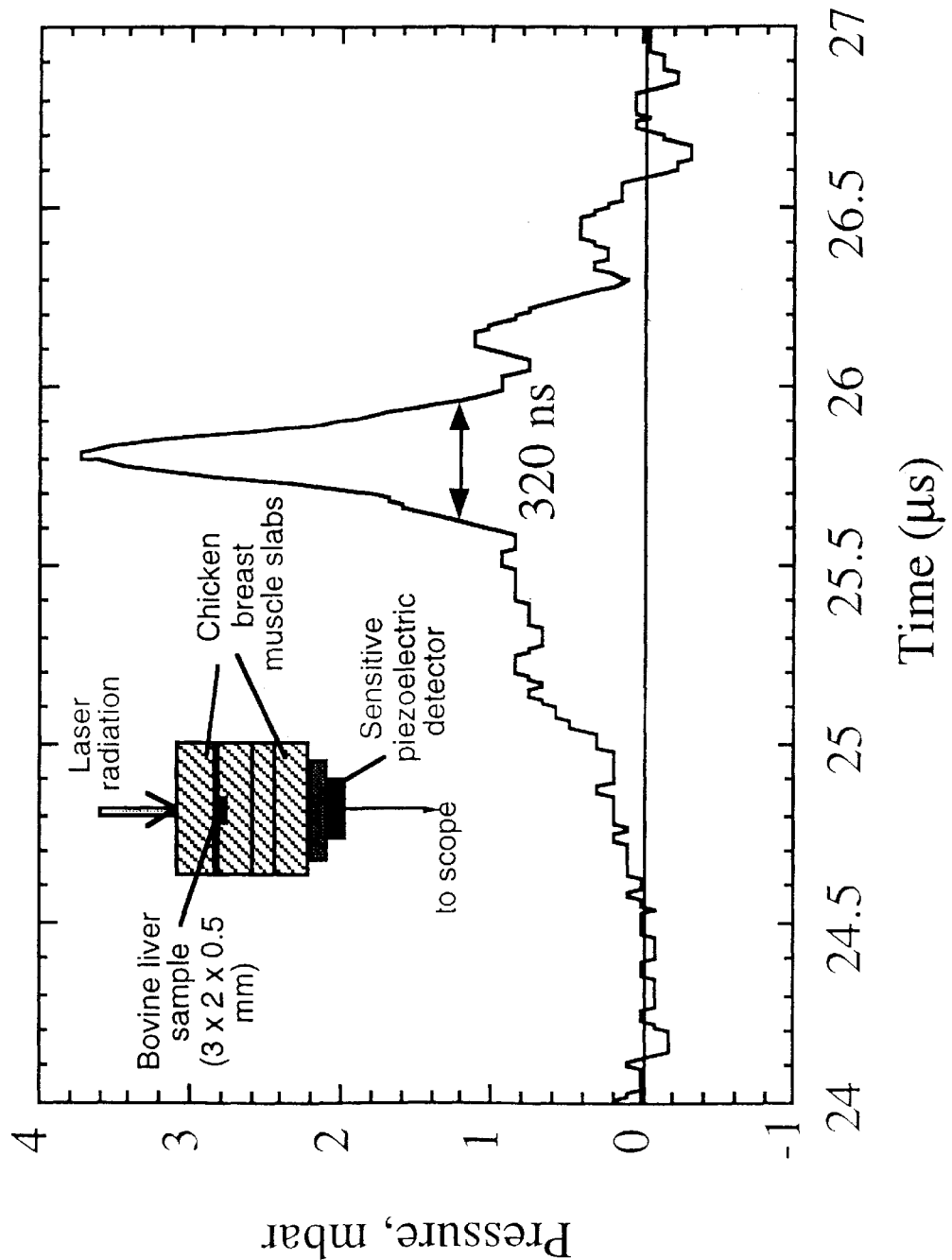
FIG. 2 shows that an acoustic transducer signal can be detected in vitro from small volume of liver placed inside large volume of chicken breast muscle tissue.

FIG. 2 depicts an example of a measurement of laser-induced transient stress in a small piece of bovine liver tissue placed between muscle tissues slabs (chicken breast). Duration of the transient stress wave and amplitude were equal to 300 ns and 4 mbar, respectively, in accordance with sample thickness and optical absorption coefficient. This experiment demonstrated the ability of laser optoacoustic tomography to detect small volumes of tissue (3 mm×2 mm×0.5 mm) with absorption coefficient, $\mu_a$=0.215 cm$^{-1}$, that is slightly higher than that of surrounding tissue, $\mu_a$=0.09 cm$^{-1}$, at the depth of more than 4 centimeters.

Figure 3:
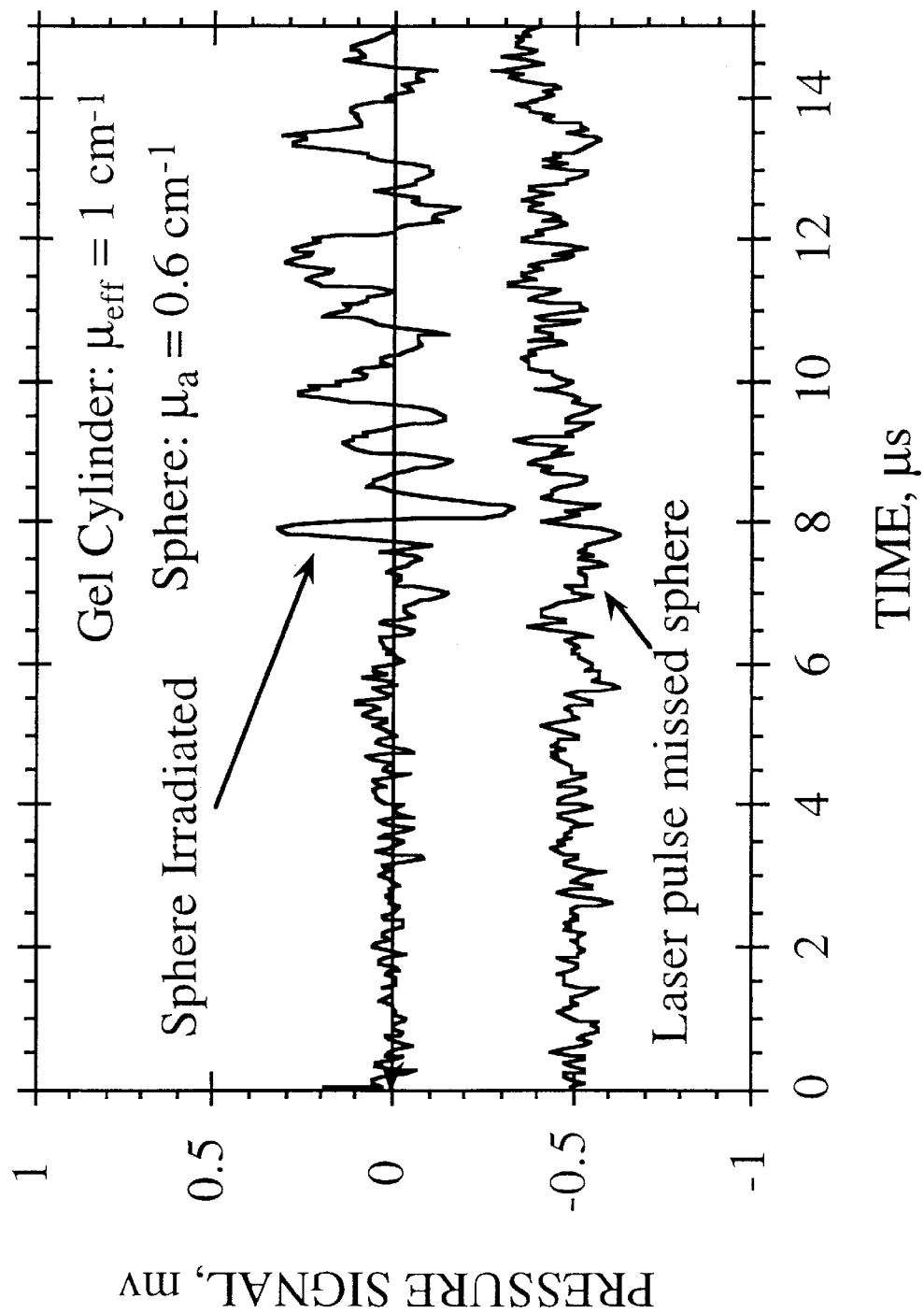
FIG. 3 shows that an acoustic transducer signal can be detected from a phantom pathologic tissue (2.5 mm colored gel sphere) embedded within large volume of optically turbid gel cylinder simulating woman's breast. Signal recorded from gel cylinder in case when laser pulse misses and therefore does not heat small color sphere is also presented for comparison.

FIG. 3 shows an acoustic transducer signal detected from a phantom pathologic tissue (2.5 mm colored gel sphere) embedded within large volume of optically turbid gel cylinder. A control signal was used in case the laser irradiation "missed" the colored sphere and is also shown. The gel phantom simulated a woman's breast by having optical properties of a colored gel sphere similar to those found in breast carcinoma. Moreover, the optical properties of the surrounding gel were similar to those in a woman's breast tissue. The geometry of the experiment is also shown. A laser pulse was delivered from one side of the gel cylinder and a transient stress wave was detected from the opposite side. The location of colored gel sphere which simulated the tumor was not known to the person who performed the diagnostic procedure. Simultaneous scanning of laser beam and acoustic transducer revealed both the location and dimensions of the "tumor".

Figure 4:
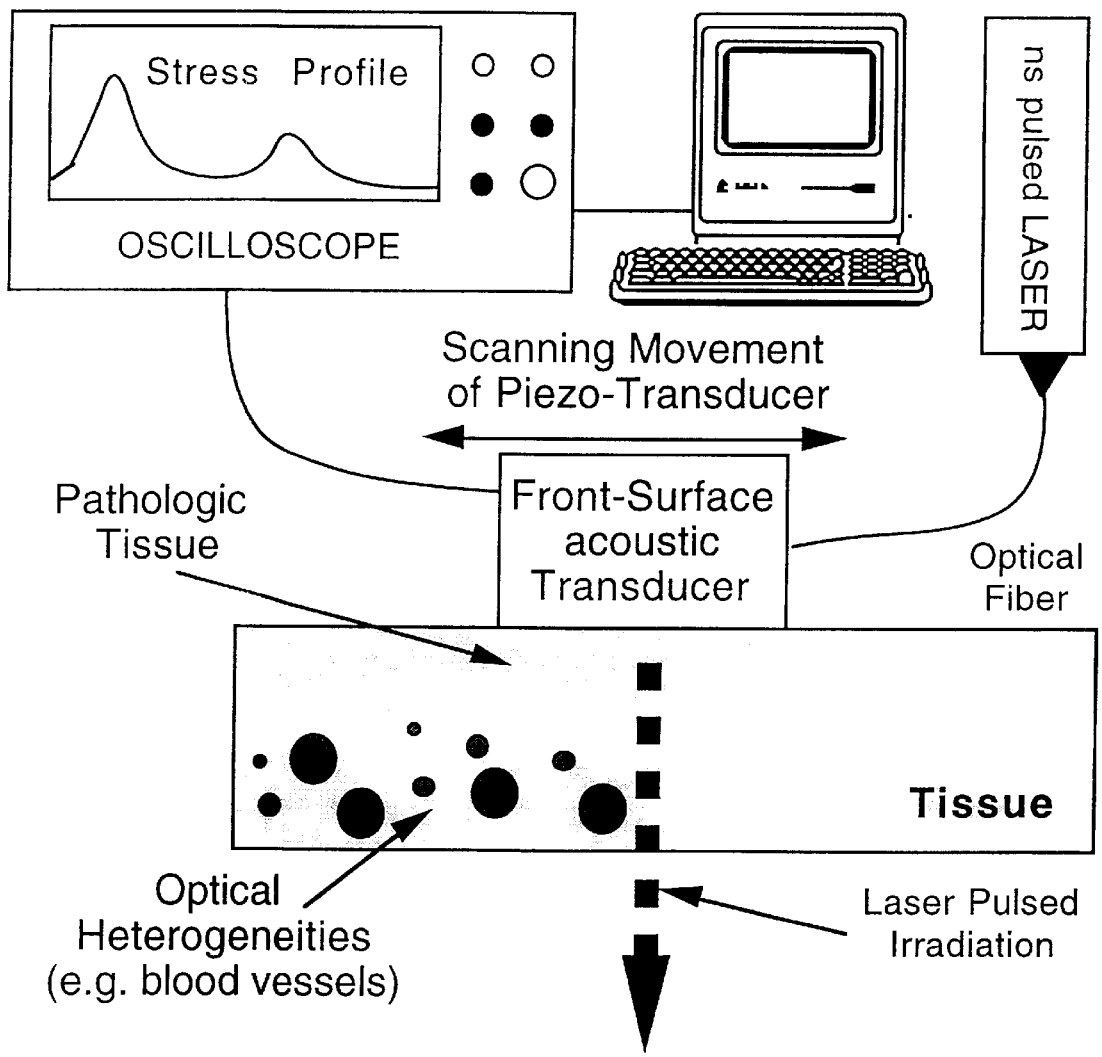
FIG. 4 shows a schematic of laser optoacoustic tomography in reflection mode.

FIG. 4 shows a schematic diagram of the laser optoacoustic tomography of the present invention in the reflection mode embodiment of stress detection. A laser pulse irradiates the surface of tissue with a wavelength chosen to penetrate the tissue superficially (about 1 mm) and to heat selectively all microstructures within the tissue with the objective of obtaining high contrast and high spatial resolution. Instantly heated volume of layered tissue produces a stress wave that has profile indicating tissue structure. Stress waves were reflected toward the irradiated surface and were detected with minimal alterations by an acoustic transducer with nanosecond temporal resolution. Laser pulses were delivered to the same tissue surface where a stress wave was detected. The amplitude and temporal profile of a laser-induced stress wave was recorded by a digital oscilloscope and transferred via an interface to a computer for data analysis. Scanning by acoustic transducer-reflectometer with the laser beam permited the irradiation of the entire area of diagnostic interest. Recorded stress profiles were analyzed by the computer to reconstruct a three dimensional image which was displayed and processed by special software.

Tomography (imaging) in stress reflection mode utilizes detection of stress transients generated in superficial tissue layer and reflected back toward tissue surface. The emphasis in reflection mode tomography is made on high spatial resolution of measured image (up to 1.5 $\mu$m).

Figure 5:
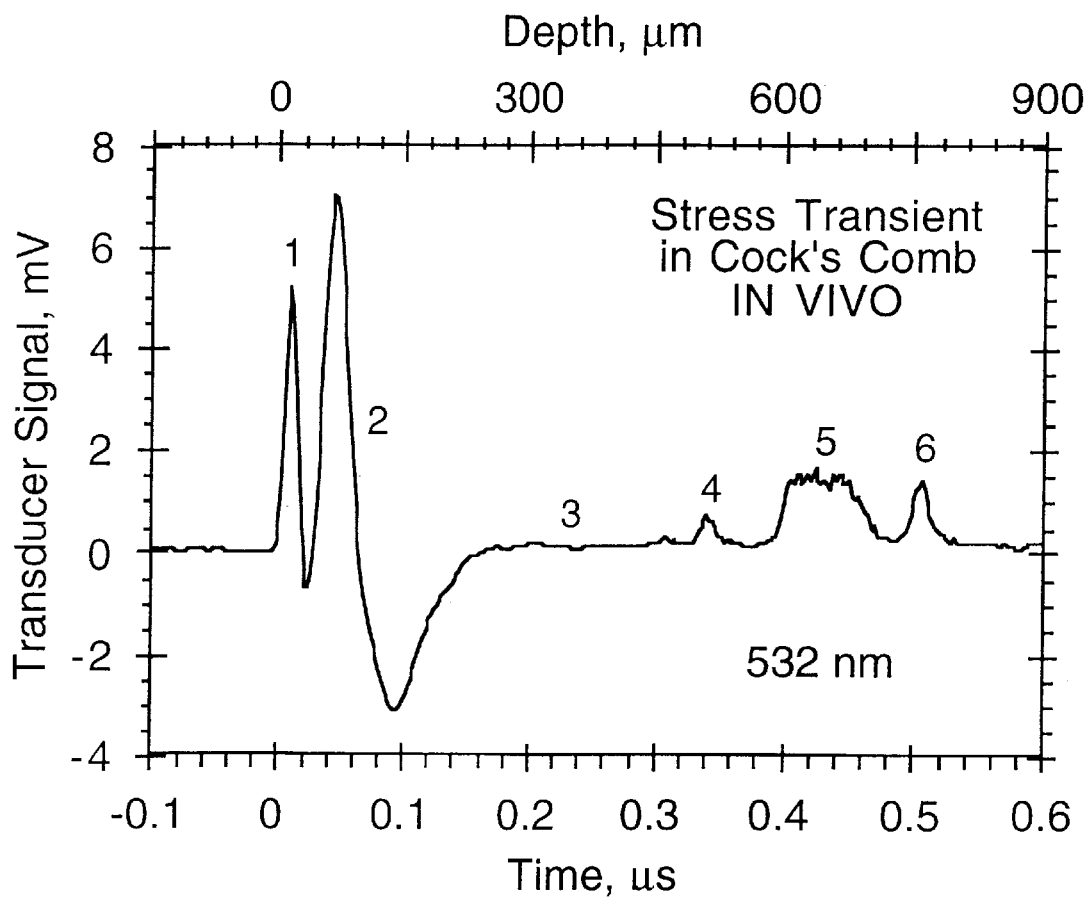
FIG. 5 shows an acoustic transducer signal detected in vivo from chicken cockscomb best known model for port-wine stains.

FIG. 5 depicts a z-axial optoacoustic image of absorbed laser fluence distribution in cock's comb. The transient stress profile induced by a 14-ns pulse at 532 nm in a cock's comb of a rooster was measured in vivo by an acoustic transducer. The laser beam was about 1 cm in diameter. Time "0" corresponds to a signal detected from the tissue surface. Distinct layers were observed in the cock's comb tissue. Alteration of the detected stress transient due to diffraction of acoustic waves generated in distributed capillary blood vessels (layer 2) yields negative signal. When diffraction effects are compensated, or the transient stress measured under diffraction-free conditions such as in a layered system with homogeneous absorption within each layer, the stress profile will have only positive components. Signals 16 were induced in blood vessels, located at different depths in the tissue. Numbers 1–5 correspond to the acoustic transducer signals detected in layers with either enhanced density of small blood vessels (1 and 2) or in separated large blood vessels (3, 4 and 5). The layered structure of the cock's comb is clearly depicted (the layer with dense small dermal blood vessels that lies just below the epidermis, the layer of less vascular loose connective tissue, the comb core layer with arteries and veins that supply the more superficial vascular layers of the cockscomb). The depth of their location is measured correctly if compared with cockscomb histology. The lateral position can be found by scanning a focused laser beam along the tissue surface.

Figure 6:
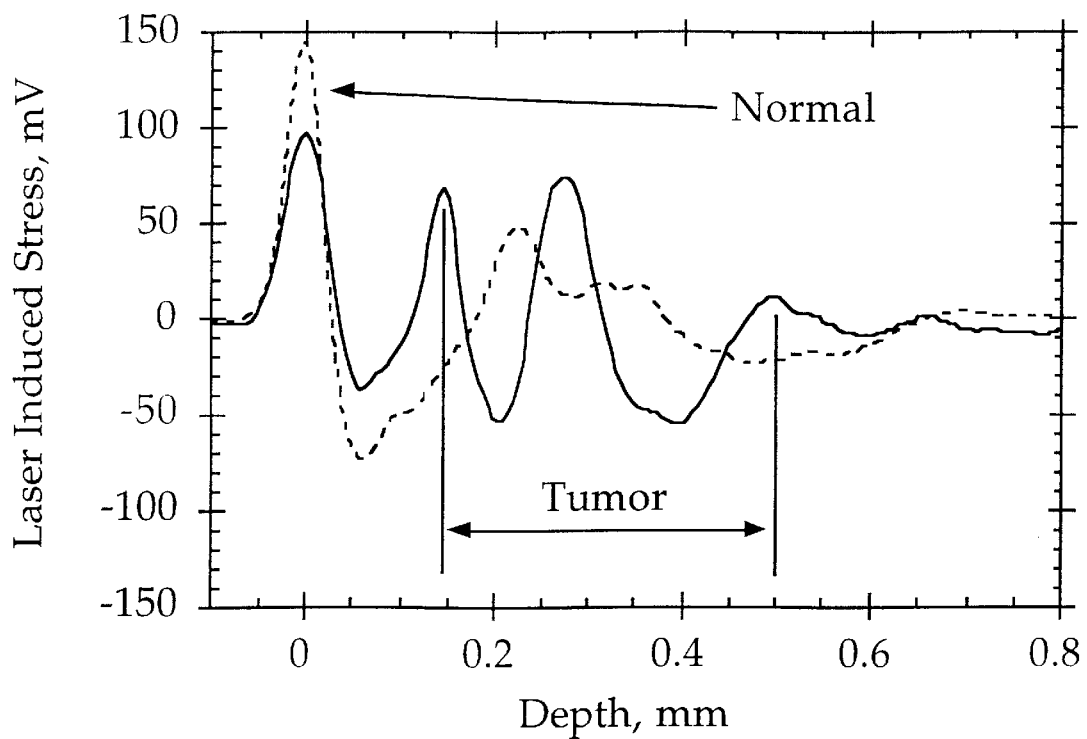
FIG. 6 shows an acoustic transducer signal detected in vivo from small tumor located underneath the skin of mouse's lower back.

FIG. 6 shows a display of a typical profile of a stress wave induced by nanosecond laser pulses at 532 nm in tissues of a mouse with a small tumor beneath the skin. Signals detected from the volume with cancer and from the tissue with no cancer are presented for comparison. The difference between two presented signals indicate that breast tumor can be diagnosed with laser optoacoustic tomography system of the present invention in a mice model in vivo. This is another example of laser optoacoustic tomography system of the present invention in the reflection embodiment performed in vivo. The object of study was a mouse with a cancer modeling female's breast tumor grown inside the muscle of the mouse. The imaging experiment was performed twice with two different mice with similar tumor conditions. These embodiments presented demonstrated laser optoacoustic imaging in tissues by time-resolved detection of laser-induced stress transients.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of characterizing a tissue using laser optoacoustic imaging, comprising the steps of:
   irradiating a volume of tissue with at least one laser pulse so as to penetrate said tissue and selectively heat a small volume or layer of said tissue with a higher optical absorption causing the tissue to produce a pressure profile confined in said volume or layer of said tissue, wherein said pressure profile reflects a value of pressure as a function of depth in said tissue, and wherein said pressure profile of said tissue is characteristic of said tissue;
   detecting said pressure profile with at least one acoustic transducer;
   recording an amplitude and temporal profile of said pressure profile by an electronic system;
   analyzing said pressure profile with a computer.

2. The method of claim 1, wherein said transducer determines a geometry of the characterized tissue volume by positioning a multiple of acoustic transducers at fixed locations along the surface of said characterized tissue.

3. The method of claim 1, wherein multiple separate optical fibers or laser beams irradiate a large volume of tissue to reduce time of scanning and incident laser fluence.

4. The method of claim 1, wherein said pressure profile detection is in forward signal propagation mode as said irradiation and said acoustic detection are performed at different sites in said tissue.

5. The method of claim 1, wherein said pressure profile detection occurs at a tissue depth of up to about 12 cm measured from an irradiated surface.

6. The method of claim 1, wherein said pressure profile detection is in backward signal propagation mode as said irradiation and said acoustic detection are performed at a same site in said tissue.

7. The method of claim 4, wherein said irradiating is in a a spectral range of from about 600 nm to about 1400 nm.

8. The method of claim 1, further comprising use of exogenous molecular probes or dyes to enhance contrast between pressure profiles of different tissues.

9. The method of claim 1, wherein said tissue is an internal organ, and wherein irradiation is delivered via an endoscope to a first tissue surface and said acoustic transducer is positioned on a second tissue surface wherein said second tissue surface is opposite said first tissue surface.

10. The method of claim 1, wherein said tissue is an internal organ, and wherein irradiation is delivered onto a first tissue surface and said transducer is incorporated with an endoscope and positioned at a second tissue surface, wherein said second tissue surface is opposite said first tissue surface.

11. The method of claim 1, wherein said tissue is an internal organ, and wherein an optical fiber and said transducer are incorporated in an endoscope and positioned inside the organ such that irradiation and detection is performed from the same site at the internal surface of said organ.

12. An imaging system for biomedical diagnostics comprising:
   a pulsed optical source to produce a pressure profile confined in a volume of tissue of diagnostic interest;
   a light delivery system for delivery of radiation to said tissue of diagnostic interest;
   at least one acoustic detector to detect said pressure profile in said volume of tissue of diagnostic interest;
   an electronic system for recording and processing of said detected pressure profile; and
   a computer with software for image reconstruction and analysis of said detected pressure profile.

13. The method of claim 12, wherein the acoustic detector is a piezoelectric or optical detector capable of detecting pressure profiles within a wide ultrasonic frequency range.

14. The method of claim 1, wherein said pressure profile is recorded simultaneously from a number of sites along a surface of said tissue in order to reconstruct a two-dimensional or three-dimensional tomographic image.

15. The method of claim 1, wherein said detecting step is performed by scanning of a single transducer along said tissue.

16. The method of claim 1, wherein said said detecting step is performed by scanning of an array of tranducers along said tissue.

17. The method of claim 1, wherein said tissue is breast cancer.

18. The method of claim 1, wherein said tissue is brain tumor tissue.

19. The method of claim 1, wherein said tissue is a hematoma.

20. The method of claim 1, wherein said tissue is atherosclerotic plaques.

21. The method of claim 1, wherein said tissue is pathologically diseased due to polyarthritis.

22. The method of claim 1, wherein said tissue is skin having vascular lesions.

23. The method of claim 1, wherein said tissue is diseased ocular tissue.

24. The method of claim 1, wherein said tissue is skin melanoma.

25. The method of claim 1, wherein said tissue is lung cancer.

26. The method of claim 1, wherein said tissue is cervical cancer.

27. The method of claim 1, wherein said tissue is prostate cancer.

28. The method of claim 1, wherein said tissue is a hollow organ selected from the group of mouth, esophagus, intestine, colon and rectum.

* * * * *